United States Patent [19]
Mittal

[11] Patent Number: 4,887,610
[45] Date of Patent: Dec. 19, 1989

[54] DEVICE TO MEASURE ELECTRICAL AND MECHANICAL EVENTS IN THE HUMAN SPHINCTERS

[75] Inventor: Ravinder K. Mittal, Charlottesville, Va.

[73] Assignee: University of Virginia Alumni Patents Foundation, Charlottesville, Va.

[21] Appl. No.: 259,595

[22] Filed: Oct. 19, 1988

[51] Int. Cl.[4] .............................................. A61B 5/10
[52] U.S. Cl. ................................... 128/733; 128/780; 128/748
[58] Field of Search ............... 128/733, 774, 778, 780, 128/748, 672–675, 734, 642, 786

[56] References Cited

U.S. PATENT DOCUMENTS

| Re. 31,377 | 9/1983 | Mylrea et al. | |
|---|---|---|---|
| 3,480,003 | 11/1969 | Crites | 128/748 X |
| 3,734,094 | 5/1973 | Calinog | |
| 3,939,823 | 2/1976 | Kaye et al. | |
| 4,063,548 | 12/1977 | Klatt et al. | 128/733 |
| 4,168,703 | 9/1979 | Kenigsberg | |
| 4,191,196 | 3/1980 | Bradley et al. | 128/733 |
| 4,224,949 | 9/1980 | Scott et al. | 128/734 |
| 4,364,239 | 12/1981 | Perlin | |
| 4,444,195 | 4/1984 | Gold | 128/786 X |
| 4,630,611 | 12/1986 | King | 128/786 X |
| 4,706,688 | 11/1987 | Michael et al. | |
| 4,776,349 | 10/1988 | Nashef et al. | 128/786 |
| 4,785,823 | 11/1988 | Eggers et al. | 128/692 |

OTHER PUBLICATIONS

Andersen et al., "Electromyographic and Gas Urethral Pressure Profile", *Neurology*, Vol. 7, No. 5, 5–1976, pp. 561–565.

Dent et al., "A New Technique for Continuous Sphincter Pressure Measurement", Gastroenterology, 71:263, 267 (U.S.A., 1976).

*Primary Examiner*—Angela D. Sykes
*Attorney, Agent, or Firm*—James C. Wray

[57] ABSTRACT

A manometric catheter which includes a sleeve device segment and attached to this sleeve device segment are two metal electrodes. This design of the manometric catheter has the capability of measuring simultaneous mechanical and electrical events in the human sphincters.

18 Claims, 1 Drawing Sheet

DEVICE TO MEASURE ELECTRICAL AND MECHANICAL EVENTS IN THE HUMAN SPHINCTERS

FIELD OF THE INVENTION

This invention relates to the measurement of pressure and electrical charges concurrently and more particularly, to physical pressure changes and electrical changes in the human sphincters. The present invention allows the measuring of mechanical and electrical events simultaneously in the human sphincters. This allows one to distinguish the site of origin of the pressure activity.

BACKGROUND OF THE INVENTION

Previous devices only measured pressure changes which occur in the human sphincters or only measured electrical changes in the cardiac region.

U.S. Pat. No. 3,480,003 is a pressure sensing apparatus for sensing esophogeal mobility around the sphincter region.

U.S. Pat. No. 3,939,823 shows an esophogeal transducer for measuring esophogeal contractions. This transducer is of a singular, circular fashion placed upon a catheter.

U.S. Pat. No. 4,168,703 discloses a tool for diagnosing a gastro-esophogeal reflex condition whereby the pressure at selected locations along the gastro-esophogeal tract in the body may be measured without disturbing the relative position of the device.

U.S. Pat. No. 4,706,688 relates to a cardiac device which is inserted into the gastro-esophogeal junction and comprises an elongated conduit having a series of electrodes for sensing or recording electrical signals of the cardiac region.

U.S. Pat. No. 4,304,239 shows an esophogeal probe with a pair of conductive electrodes being connected to the distal end of the probe's shaft to make improved contact with the patient's body on the esophagus to sense ECG waves.

U.S. Pat. No. 3,734,094 describes a multipurpose esophogeal instrument which is capable of withdrawing fluids and monitoring the heart simultaneously or in succession.

U.S. Pat. No. Re. 31,377 shows an esophogeal probe incorporating the capability to detect ECG waveforms, heart sounds, and to measure body core temperature.

Two other devices which record lower esophogeal sphincter pressure are the side-hole manometry and the Dent sleeve device.

SUMMARY OF THE INVENTION

The pressure in the human lower esophogeal sphincter and anal sphincter can be the result of either the smooth or skeletal muscle contraction. To distinguish the site of origin of this pressure activity an instrument must measure the EMG (electromyogram) activity of the skeletal muscle along with the pressure measurement.

Prior art devices measure either pressure or ECG (electrocardiogram). None of these prior art devices allow for simultaneously measuring mechanical and electrical events in the human sphincters.

The present invention allows simultaneously measuring physical pressure changes and electrical changes in a sphincter and comprises a catheter which has a pressure sensing means for sensing pressure changes and electrical sensing means for sensing electrical changes.

Preferably, the pressure sensing means is a sleeve device.

In one embodiment of the present invention the electrical sensing means is bipolar electrodes.

When a sleeve device is used, these bipolar electrodes are placed 1 cm apart and the first electrode is spaced 1 cm from the proximal margin of the sleeve.

In one embodiment of the invention, the bipolar electrodes are metal foil squares. Two Teflon-coated, insulated metal wires are guided through one of the side holes of the manometric catheter and externalized at a proximal end of the catheter. The distal ends of the wires have the insulation removed up to 0.5 cm from the tips and the insulated tips are attached to an undersurface of the metal foils. These wires can be arc-welded to the undersurface of the metal foils.

In another embodiment of the present invention, the bipolar electrodes consist of uninsulated metal wire wound around the catheter.

In another embodiment of the present invention, the electrical sensing means consists of two long parallel electrodes which are at least as long as the sleeve device and are made up of an uninsulated metal wire coil and are attached to the outside walls of the sleeve device.

These and other and further objects and features of the invention are apparent in the disclosure which includes the above and ongoing specification with the drawings and the claims.

DETAILED DESCRIPTION OF THE INVENTION

Figure 1:
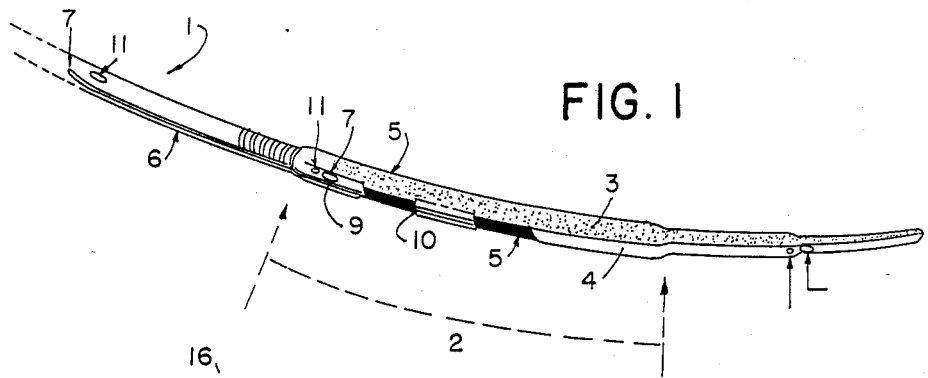
FIG. 1 is a top perspective view of one embodiment of the present invention.

Referring now to the drawings, reference numeral 1 is used to generally designate the manometric catheter with the capability of measuring simultaneous mechanical and electrical events in the human sphincters. For simplicity, the whole catheter is not shown. The catheter includes a sleeve device segment 2 which has an almost tubular structure and its anatomy is such that only one-quarter of its circumference is utilized as a pressure sensing surface 3 and the remaining three-quarters serve as a supporting structure 4. Two thin metal foil squares 5, 0.05 mm thick and 1 cm$^2$ in surface area, are glued with silicon rubber glue to the supporting structure 4 of the sleeve device. These electrodes 5 are placed 1 cm apart, and the proximal one is spaced 1 cm from the proximal margin of the sleeve device 2. Two Teflon-coated, insulated metal wires 6 are guided through one of the side holes 7 of the manometric catheter 1 to be externalized at the proximal end of the catheter. At their distal ends, the insulation 9 was removed up to 0.5 cm from the tips, and the wires are arc-welded to the undersurface 10 of the metal foils 5. The manometric catheter 1 has side ports 7 and metal inserts 11 spaced along its length.

Figure 2:
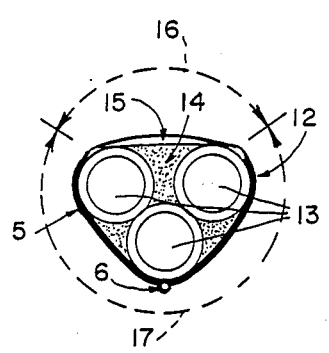
FIG. 2 is an enlarged cross-sectional view of the Dent sleeve segment of the present invention.

FIG. 2 shows an enlarged cross section of the preferred sleeve device 12. This preferred sleeve device 12 is known as the Dent sleeve. The method of construction of the Dent sleeve device 12 is fully described in the article entitled "A New Technique for Continuous Sphincter Pressure Measurement," found in *Gastroenterology*, 71, 263-267 (1976). Generally, the sleeve 15 consists of silicon rubber sheets, unreinforced 0.13 mm thick and Dacron-reinforced 0.18 mm thick which are glued together and trimmed. A gluing bed for the sleeve 15 is made by gluing together three 70 cm long silicon rubber tubes 13 of 2.41 mm external diameter and 1.57 mm internal diameter. These tubes 13 are accurately spaced as to provide a gutter between two of the tubes and this gutter is filled with silicon rubber glue 14 to produce the gluing bed for which the sleeve 15 is attached. Sleeve 15 is glued along the length of the bed with the Dacron-reinforced side downwards. FIG. 2 also shows the metal foil squares 5 glued to the preferred sleeve device 12 and the insulated metal wires 6 arc-welded to the undersurface of the metal foils 5. FIG. 2 also illustrates the pressure sensing surface 16 and non-pressure sensing surface 17 of the present invention.

Figure 3:
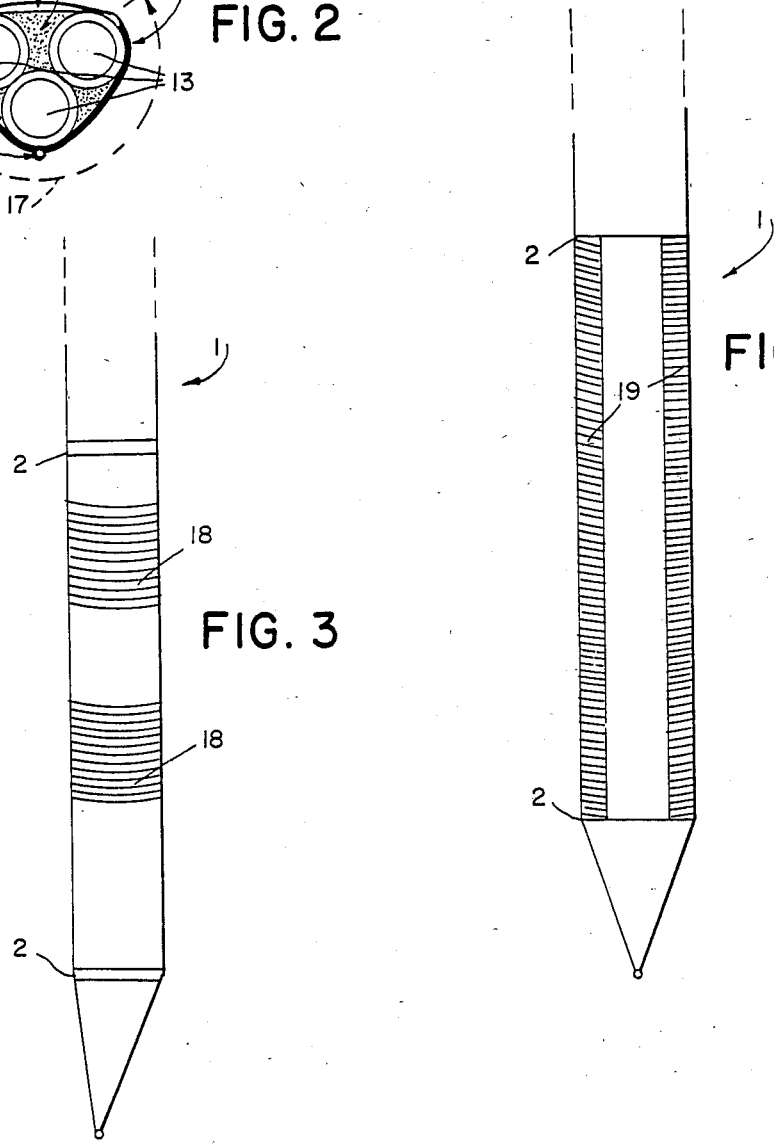
FIG. 3 shows uninsulated metal wire electrodes attached to the sleeve device of the present invention.

FIG. 3 shows uninsulated metal wire electrodes 18 attached to the sleeve device of the present invention. Uninsulated wire 18 is wound around the sleeve device 2 so that each of the two bipolar electrodes are 1 cm² in surface area. Again, these wire electrodes are spaced 1 cm apart, and the proximal one is spaced 1 cm from the proximal margin of the sleeve device 2.

Figure 4:
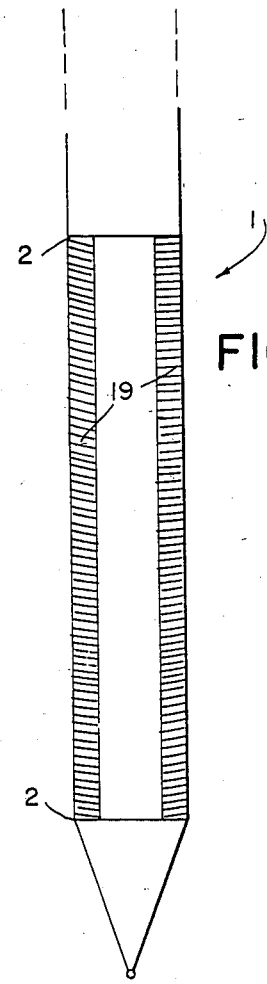
FIG. 4 illustrates another version of attaching the uninsulated metal wire electrodes.

FIG. 4 illustrates another version of attaching the uninsulated wire metal electrodes 19 to the sleeve device of the present invention. In this embodiment the electrodes consist of two long and narrow wire coils which extend the length of the sleeve device. The design of the electrodes attached to the sleeve device is such that the electrodes do not extend beyond the width of the catheter.

Any metal with good electrical conductivity can be used for the electrodes. In the past, platinum has been used in the construction of this invention. The arrangement of the electrodes is especially important when the device is used to record simultaneously the lower esophogeal sphincter pressure and the diaphragmic electromyogram, since the best diaphragmic electromyogram is recorded when the electrodes are located as close to the diaphragm as possible.

While the invention has been described with reference to specific embodiments, modifications and variations of the invention may be made without departing from the scope of the invention which is defined by the following claims.

I claim:

1. A device for measuring physical pressure charges and electrical changes in a sphincter comprising a catheter which has a pressure sensing means for sensing pressure changes and electrical sensing means for sensing electrical changes, wherein the pressure sensing means and the electrical sensing means are located in a same area on the catheter, but on different sides of the catheter so that the measuring of physical changes and electrical changes take place simultaneously at a given point of the sphincter.

2. The device of claim 1, wherein the pressure sensing means is a sleeve device.

3. The device of claim 2, wherein the electrical sensing means is bipolar electrodes which are placed 1 cm apart and wherein a first electrode is spaced 1 cm from a proximal margin of the sleeve device.

4. The device of claim 3, wherein the bipolar electrodes are metal foil squares, and wherein two Teflon-coated, insulated metal wires are guided through a side hole of a manometric catheter wherein proximal ends of the wires are externalized at a proximal end of the catheter and distal ends of the wires have the insulation removed up to 0.5 cm from tips of the wire and the uninsulated tips are attached to an undersurface of the metal foil squares.

5. The device of claim 4, wherein the metal used for the foil squares and the wires is platinum.

6. The device of claim 4, wherein the wires are arc-welded to the undersurface of the metal foil squares.

7. The device of claim 3, wherein the bipolar electrodes consist of uninsulated metal wire wound around the catheter wherein each electrode has a surface area of at least 1 cm².

8. The device of claim 2, wherein the electrical sensing means consists of two long parallel electrodes which are at least as long as the sleeve device and are made up of an uninsulated metal wire coil and are attached to outside walls of the sleeve device.

9. The device of claim 1, wherein the electrical sensing means is bipolar electrodes.

10. A device for measuring physical pressure changes and electrical changes in a sphincter, comprising:
    a catheter having a pressure sensing means for sensing pressure changes and an electrical sensing means for sensing electrical changes;
    wherein the pressure sensing means and the electrical sensing means are located in a same area of the catheter, and
    wherein further the pressure sensing means occupies one-fourth of a circumference of the catheter and the electrical sensing means occupies a remaining three-fourths of the circumference of the catheter so that the catheter simultaneously measures pressure and electrical changes at a given point of the sphincter.

11. The device of claim 10, wherein the pressure sensing means is a sleeve device.

12. The device of claim 11, wherein the electrical sensing means is bipolar electrodes which are placed 1 cm. apart and wherein a first electrode is spaced 1 cm. from a proximal margin of the sleeve device.

13. The device of claim 12, wherein the bipolar electrodes are metal foil squares, and wherein two Teflon-coated, insulated metal wires are guided through a side hole of a manometic catheter wherein proximal ends of the wires are externalized at a proximal end of the catheter and distal ends of the wires have the insulation removed up to 0.5 cm. from tips of the wire and the uninsulated tips are attached to an undersurface of the metal foil squares.

14. The device of claim 13, wherein the metal used for the foil squares and the wires is platinum.

15. The device of claim 13, wherein the wires are arc-welded to the undersurface of the metal foil squares.

16. The device of claim 12, wherein the bipolar electrodes consist of uninsulated metal wire wound around the catheter wherein each electrode has a surface area of at least 1 cm².

17. The device of claim 11, wherein the electrical sensing means consists of two long parallel electrodes which are at least as long as the sleeve device and are made up of an uninsulated metal wire coil and are attached to outside walls of the sleeve device.

18. The device of claim 10, wherein the electrical sensing means is bipolar electrodes.

* * * * *